United States Patent
Zhu et al.

(10) Patent No.: US 12,104,128 B2
(45) Date of Patent: *Oct. 1, 2024

(54) APPARATUS TO SIMULATE BIOCIDE PERFORMANCE IN CRUDE PIPELINE CONDITIONS

(71) Applicant: SAUDI ARABIAN OIL COMPANY, Dhahran (SA)

(72) Inventors: Xiangyang Zhu, Dhahran (SA); Mazen A. Al-Saleh, Khobar (SA); Qurban Ali, Khobar (SA)

(73) Assignee: SAUDI ARABIAN OIL COMPANY, Dhahran (SA)

(*) Notice: Subject to any disclaimer, the term of this patent is extended or adjusted under 35 U.S.C. 154(b) by 0 days.

This patent is subject to a terminal disclaimer.

(21) Appl. No.: 18/340,420

(22) Filed: Jun. 23, 2023

(65) Prior Publication Data

US 2023/0383202 A1    Nov. 30, 2023

Related U.S. Application Data

(62) Division of application No. 16/572,206, filed on Sep. 16, 2019, now Pat. No. 11,718,801.

(51) Int. Cl.
*C10G 75/02* (2006.01)
*B01J 19/18* (2006.01)
(Continued)

(52) U.S. Cl.
CPC .............. *C10G 75/02* (2013.01); *B01J 19/18* (2013.01); *C12M 37/06* (2013.01); *C12M 41/38* (2013.01);
(Continued)

(58) Field of Classification Search
None
See application file for complete search history.

(56) References Cited

U.S. PATENT DOCUMENTS 4,309,899 A    1/1982  Torres
9,732,369 B2   8/2017  Pilloni et al.
(Continued)

FOREIGN PATENT DOCUMENTS

CN    2700870 Y    5/2005
CN    1690689 A    11/2005
(Continued)

OTHER PUBLICATIONS

Dickinson, Wayne et al., "Tank Reactor Studies of Biocide Performance and Mitigation of Dead-leg Corrosion." Corrosion 2012. OnePetro, 2012. 7 pages.
(Continued)

*Primary Examiner* — William H. Beisner
(74) *Attorney, Agent, or Firm* — Leason Ellis LLP

(57) ABSTRACT

An apparatus to simulate biocide performance in crude oil pipeline conditions is disclosed. The apparatus includes: a reactor to simulate a two-phase crude oil pipeline which includes a crude oil phase above a water phase. The reactor has an agitator to control a flow of the water phase in the reactor in response to a motor that drives an agitation rate of the agitator. A crude oil inlet supplies crude oil to the reactor for the crude oil phase. A water inlet supplies water to the reactor for the water phase. A control circuit is configured by code to control a proportion of the water to the crude oil supplied to the reactor and to control the motor to drive a desired agitation rate of the agitator. A biocide inlet supplies biocide to the reactor. A water sample outlet enables sampling of the water phase of the reactor.

16 Claims, 8 Drawing Sheets

(51) Int. Cl.
*C12M 1/02* (2006.01)
*C12M 1/12* (2006.01)
*C12M 1/34* (2006.01)

(52) U.S. Cl.
CPC .............. *B01J 2219/00164* (2013.01); *B01J 2219/00189* (2013.01); *B01J 2219/00245* (2013.01); *C10G 2300/208* (2013.01); *C10G 2300/80* (2013.01); *C12M 1/02* (2013.01); *C12M 1/121* (2013.01)

(56) References Cited

U.S. PATENT DOCUMENTS

| | | | |
|---|---|---|---|
| 11,718,801 B2* | 8/2023 | Zhu | B01J 19/18 73/865.6 |
| 2010/0212888 A1 | 8/2010 | Suchezky et al. | |
| 2012/0311922 A1 | 12/2012 | Tinetti et al. | |
| 2015/0119286 A1 | 4/2015 | Whitfield et al. | |
| 2016/0360749 A1 | 12/2016 | He et al. | |
| 2018/0051309 A1 | 2/2018 | Pilloni et al. | |
| 2019/0056305 A1 | 2/2019 | Aljanabi et al. | |
| 2021/0018425 A1 | 1/2021 | Alanazi | |

FOREIGN PATENT DOCUMENTS

| | | |
|---|---|---|
| CN | 100526845 C | 8/2009 |
| CN | 102854122 A | 1/2013 |
| CN | 203178166 U | 9/2013 |
| CN | 103728439 A | 4/2014 |
| CN | 103926191 A | 7/2014 |
| CN | 104483448 A | 4/2015 |
| CN | 104502532 A | 4/2015 |
| CN | 104502556 A | 4/2015 |
| CN | 104749090 A | 7/2015 |
| CN | 107179274 A | 9/2017 |
| CN | 108627618 A | 10/2018 |
| CN | 109520919 A | 3/2019 |
| WO | 2006030226 A1 | 3/2006 |
| WO | 2019035145 A1 | 2/2019 |

OTHER PUBLICATIONS

Written Opinion of the International Preliminary Examining Authority No. PCT/US2020/050872 mailed May 28, 2021. 11 pages.
Muthukumar N. et al., "Water-soluble inhibitor on microbiologically influenced corrosion in diesel pipeline." Colloids and Surfaces B: Biointerfaces 53.2 (2006): 260-270.
Kathy Riggs Larsen, Managing corrosion of pipelines that transport crude oils, Materials Performance (MP), NACE International, vol. 52, No. 5, 2013.
Xiaoqin Song, Yuexin Yang, Dongliang Yu, Guihong Lan, Zhilin Wang, Xingjie Mou. 2016. Studies on the impact of fluid flow on the microbial corrosion behavior of product oil pipelines. Journal of Petroleum Science and Engineering. vol. 146, Oct. 2016, p. 803-812. https://doi.org/10.1016/j.petrol.2016.07.035.
Eckert, R.B., 2015. Emphasis on biofilms can improve mitigation of microbiologically influenced corrosion in oil and gas industry. Corros. Eng. Sci. Technol., vol. 50, p. 163-168. https://doi.org/10.1179/1743278214Y.0000000248.
Mazen A. Al-Saleh, Peter F. Sanders, Tawfiq M. Ibrahim, Ketil Bernt Sørensen, Thomas Lundgaard, Susanne Juhler. Microbially influenced corrosion assessment in crude oil pipelines. Paper No. NACE-11227. NACE International, Corrosion 2011, Mar. 13-17, Houston, Texas.
International Search Report and Written Opinion in Corresponding PCT Application No. PCT/US2020/050872 mailed Jan. 13, 2021. 17 pages.
International Preliminary Report on Patentability in corresponding PCT Application No. PCT/US2020/050872; issued on Oct. 18, 2021; 28 pages.

* cited by examiner

APPARATUS TO SIMULATE BIOCIDE PERFORMANCE IN CRUDE PIPELINE CONDITIONS

CROSS-REFERENCE TO RELATED APPLICATION

This application is a divisional of, and claims priority from, now-allowed U.S. patent application Ser. No. 16/572,206, titled APPARATUS TO SIMULATE BIOCIDE PERFORMANCE IN CRUDE PIPELINE CONDITIONS, filed on Sep. 16, 2019, which is hereby incorporated by reference in its entirety.

FIELD OF THE DISCLOSURE

The present disclosure relates in general to crude pipeline simulation technologies, and in particular to an apparatus to simulate biocide performance in crude pipeline conditions.

BACKGROUND OF THE DISCLOSURE

Crude oil (such as sweet crude, averaging less than 0.5% sulfur) is often transported by a metallic pipeline. During the pipeline transportation process, water and solids naturally present in the crude can drop out of the solution and deposit or form a separate flow (e.g., a two-phase flow) on the bottom of the pipeline's interior. These drop outs can accumulate at low points in the pipeline due to low flow velocity or even stagnant flow. As such, the drop outs can become a breeding ground for corrosion, such as microbial corrosion, and other microbiologically influenced corrosion (MIC) effects in crude oil pipelines.

Uncontrolled microbial activity, and the consequent microbial corrosion, is one of the leading causes of pipeline failure in the oil industry. The processed crude oil normally only contains very low "basic sediment and water" (BS&W) (such as less than 1%) as required by oil transmission pipeline tariffs. This small amount of water, when kept off the pipeline wall and entrained in the crude oil, should not pose high microbial corrosion risks to the crude pipelines. However, when oil production decreases, and as a consequence, the flow rate decreases in the crude pipelines, the trace water and sediments can drop out of the crude oil and accumulate at low-lying sections of the pipelines, causing under-deposit corrosion and microbial corrosion.

It is in regard to these and other problems in the art that the present disclosure is directed to provide a technical solution for effective simulation of biocide and other oil field chemical treatment in crude pipeline conditions.

SUMMARY OF THE DISCLOSURE

According to an embodiment, an apparatus to simulate biocide performance in crude oil pipeline conditions is provided. The apparatus includes: a reactor to simulate a two-phase crude oil pipeline and including a crude oil phase above a water phase, the reactor including an agitator to control a flow of the water phase in the reactor in response to a motor that drives an agitation rate of the agitator; a crude oil inlet to supply crude oil to the reactor for the crude oil phase; a water inlet to supply water to the reactor for the water phase; a control circuit configured by logic or code to control a proportion of the water to the crude oil supplied to the reactor by the crude oil inlet and the water inlet, and to control the motor to drive a desired agitation rate of the agitator; a biocide inlet to supply biocide to the reactor; and a water sample outlet to sample the water phase of the reactor.

In an embodiment, the reactor further includes a plurality of reactors each having a dedicated said biocide inlet and a dedicated said water sample outlet, and the control circuit is further configured by logic or code to independently control the proportion of the water to the crude oil and to independently control the motor in each reactor.

In an embodiment, the apparatus further includes: a crude oil pump to pump the crude oil from a crude oil supply to the crude oil inlet; and a water pump to pump the water from a water supply to the water inlet, wherein the control circuit controls the proportion of the water to the crude oil by controlling the crude oil pump and the water pump.

In an embodiment, the apparatus further includes a plurality of coupon holders each configured to hold a corrosion coupon at a bottom of the agitated water phase of the reactor during a simulation, and to permit removing and replacing of the corrosion coupon during the simulation.

In an embodiment, the apparatus further includes a ball valve for each coupon holder, the ball valve being configured to seal the reactor during the removal and replacement of the corrosion coupon.

In an embodiment, the reactor further includes a bucket and the agitator includes a rotor at the bottom of the bucket, the agitation rate being a rotation speed of the rotor, and the control circuit further controls the motor to adjust a height of the rotor above the bottom of the bucket.

In an embodiment, the apparatus further includes a height-adjustable dip tube to obtain a mixed sample of the crude oil phase and the water phase of the reactor at an interphase region of the crude oil phase and the water phase in the reactor.

In an embodiment, the apparatus further includes a heating element to heat the reactor and a temperature sensor to sense a temperature of the reactor, wherein the control circuit is further configured by logic or code to control the temperature of the reactor by using the temperature sensor to sense the temperature of the reactor and by using the heating element to heat the reactor in response to the sensed temperature.

According to another embodiment, an apparatus to simulate oil field chemical performance in crude oil pipeline conditions is provided. The apparatus includes: a plurality of reactors each configured to simulate a two-phase crude oil pipeline and including a crude oil phase above a water phase, each reactor including an agitator to control a flow of the water phase in the reactor in response to a motor that drives an agitation rate of the agitator; a crude oil inlet to supply crude oil to each reactor for the crude oil phase; a water inlet to supply water to each reactor for the water phase; a control circuit configured by logic or code to independently control a proportion of the water to the crude oil supplied to each reactor by the crude oil inlet and the water inlet, and to independently control the motor of each reactor to drive a desired agitation rate of the agitator of the reactor; a dedicated oil field chemical inlet for each reactor to supply an oil field chemical to the reactor; and a dedicated water sample outlet for each reactor to sample the water phase of the reactor.

In an embodiment, the oil field chemical includes at least one of a corrosion inhibitor and a biocide.

In an embodiment, the apparatus further includes: a crude oil pump to pump the crude oil from a crude oil supply to the crude oil inlet; and a water pump to pump the water from a water supply to the water inlet, wherein the control circuit controls the proportion of the water to the crude oil by controlling the crude oil pump and the water pump.

In an embodiment, each reactor further includes a plurality of coupon holders each configured to hold a corrosion coupon at a bottom of the agitated water phase of the reactor during a simulation, and to permit removing and replacing of the corrosion coupon during the simulation.

In an embodiment, the apparatus further includes a ball valve for each coupon holder, the ball valve being configured to seal the reactor during the removal and replacement of the corrosion coupon.

In an embodiment, each reactor further includes a bucket and the agitator includes a rotor at the bottom of the bucket, the agitation rate being a rotation speed of the rotor, and the control circuit further controls the motor of each reactor to adjust a height of the rotor above the bottom of the bucket of the reactor.

In an embodiment, the apparatus further includes a dedicated height-adjustable dip tube for each reactor to obtain a mixed sample of the crude oil phase and the water phase of the reactor at an interphase region of the crude oil phase and the water phase in the reactor.

In an embodiment, the apparatus further includes a dedicated heating element for each reactor to heat the reactor and a dedicated temperature sensor for each reactor to sense a temperature of the reactor, wherein the control circuit is further configured by logic or code to independently control the temperature of each reactor by using the temperature sensor to sense the temperature of the reactor and by using the heating element to heat the reactor in response to the sensed temperature.

According to another embodiment, a method to simulate biocide performance in crude oil pipeline conditions is provided. The method includes: simulating a two-phase crude oil pipeline in a reactor including a crude oil phase above a water phase; controlling, using a processing circuit, a flow of the water phase in the reactor by controlling a motor of an agitator to drive a desired agitation rate of the agitator to agitate the water phase; supplying, using the processing circuit, crude oil to the reactor for the crude oil phase; supplying, using the processing circuit, water to the reactor for the water phase to reach a desired proportion of the water to the crude oil supplied to the reactor; supplying, through a biocide inlet, biocide to the reactor; and sampling, through a water sample outlet, the water phase of the reactor.

In an embodiment, the reactor further includes a plurality of reactors, controlling the flow of the water phase includes independently controlling the flow of the water phase in each reactor by controlling the motor of the agitator to drive the desired agitation rate of the agitator of the reactor, supplying the crude oil to the reactor includes independently supplying the crude oil to each reactor, and supplying the water to the reactor includes independently supplying the water to each reactor to reach the desired proportion of the water to the crude oil supplied to the reactor.

In an embodiment, the reactor further includes a plurality of reactors each having a dedicated said biocide inlet and a dedicated said water sample outlet, supplying the biocide to the reactor includes independently supplying, through the dedicated biocide inlet of each reactor, the biocide to the reactor, and sampling the water phase of the reactor includes independently supplying, through the dedicated water sample outlet, the water phase of the reactor.

In an embodiment, the method further includes removing and replacing a corrosion coupon at a bottom of the agitated water phase of the reactor during a simulation.

In an embodiment, the reactor further includes a bucket and the agitator includes a rotor at the bottom of the bucket, the agitation rate being a rotation speed of the rotor, and controlling the motor further includes controlling the motor to adjust a height of the rotor above the bottom of the bucket.

According to another embodiment, a method to simulate oil field chemical performance in crude oil pipeline conditions is provided. The apparatus includes: independently simulating a two-phase crude oil pipeline in each of a plurality of reactors each including a crude oil phase above a water phase; independently controlling, using a processing circuit, a flow of the water phase in each reactor by independently controlling a motor of an agitator of each reactor to drive a desired agitation rate of the agitator of the reactor to agitate the water phase of the reactor; independently supplying, using the processing circuit, crude oil to each reactor for the crude oil phase of the reactor; independently supplying, using the processing circuit, water to each reactor for the water phase of the reactor to reach a desired proportion of the water to the crude oil supplied to the reactor; independently supplying, through a dedicated oil field chemical inlet of each reactor, an oil field chemical to the reactor; and independently sampling, through a dedicated water sample outlet of each reactor, the water phase of the reactor.

In an embodiment, the oil field chemical includes at least one of a corrosion inhibitor and a biocide.

In an embodiment, independently supplying the oil field chemical includes supplying the corrosion inhibitor to one of reactors and supplying the biocide to another one of the reactors.

In an embodiment, independently supplying the oil field chemical further includes supplying both the corrosion inhibitor and the biocide to yet another one of the reactors.

In an embodiment, the method further includes removing and replacing a corrosion coupon at a bottom of the agitated water phase of each reactor during a simulation in the reactor.

In an embodiment, each reactor further includes a bucket and the agitator of each reactor includes a rotor at the bottom of the bucket, the agitation rate being a rotation speed of the rotor, and independently controlling the motor includes independently controlling the motor of each reactor to adjust a height of the rotor above the bottom of the bucket of the reactor.

Any combinations of the various embodiments and implementations disclosed herein can be used. These and other aspects and features can be appreciated from the following description of certain embodiments along with the accompanying drawings and claims.

Figure 1:
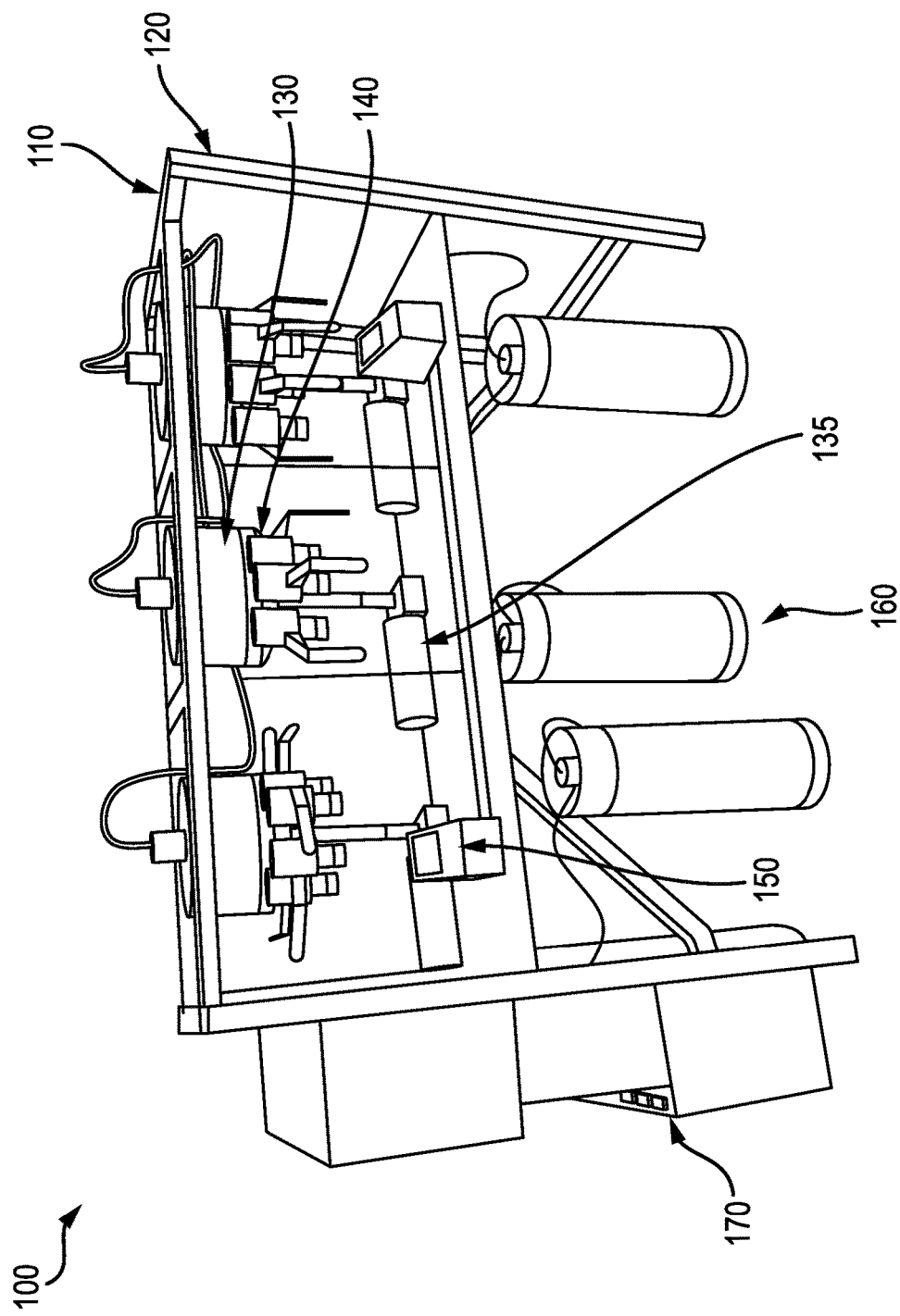
FIG. 1 is an illustration of an example three-reactor apparatus to simulate biocide performance in crude pipeline conditions, according to an embodiment.

It is noted that the drawings are illustrative and not necessarily to scale.

DETAILED DESCRIPTION OF CERTAIN EMBODIMENTS OF THE DISCLOSURE

Example embodiments of the present disclosure are directed to an apparatus to simulate crude pipeline conditions, evaluate biocide performance in such conditions, and improve or optimize biocide treatment strategy for such conditions. In an embodiment, a laboratory biocontrol simulator apparatus is provided. The apparatus is designed to simulate a two-phase crude oil pipeline (including layered oil and water fluid phases) and evaluate biocide performance against microbial corrosion (such as from harmful biofilms) in such a pipeline. To this end, the apparatus simulates biofilm growth on the interior surface of the pipeline and provides for biocide treatment of such growth. The apparatus is further to improve or optimize biocide treatment strategies against biofilm and other microbial corrosion in such a crude oil pipeline under various water cuts (or water concentrations in the crude oil) and flow conditions. The apparatus is further to assess microbial corrosion due to microbial activities in the biofilm.

Microbial corrosion in crude pipelines can be addressed in a variety of ways, such as proper pipeline design, physical mitigation, and chemical mitigation. Ideally, a pipeline should be designed to maintain a turbulent flow regime, such as maintaining the flow rates above the critical entrainment velocity. The pipeline should also avoid deadlegs (isolated sections of the pipeline that do not usually carry a flow). Further, the pipeline should be designed to prevent the settling of water droplets and solid particles at the bottom of the pipe (e.g., 6 o'clock position). Further, the pipeline should be scraped periodically to disrupt and remove any solids and water from the pipe surface. In addition, after scraping, corrosion inhibitors or biocides can be applied to treat the pipe surface and control microbial activities. Nevertheless, the water cut (e.g., proportion of water) of crude oil increases over time and the processed crude sometimes does not meet the "basic sediment and water" (BS&W) limit. In addition, crude pipelines are often overdesigned (e.g., having excess capacity), resulting in low average flow velocity, which leads to increased water and solids dropout.

While scraping is a common practice to mitigate the crude pipeline corrosion, some pipelines are not accessible to scraping pigs due to design restrictions. In addition, while biocides offer possible mitigation to microbial corrosion (such as from biofilms) in crude oil pipelines, evaluating biocide performance and optimizing the biocide treatment strategies under crude pipeline conditions can be challenging. This is due to factors such as the impracticality of testing biocide treatment on actual crude oil pipelines (e.g., field tests) and the difficulty of adequately simulating crude pipeline environments on a much smaller (e.g., laboratory) scale. For example, microbial corrosion in crude oil pipelines varies significantly depending on factors such as environment, type of crude oil, water content in the crude oil (water cut), flow rates, to name a few. Thus, it can be difficult to evaluate biocide performance and optimize biocide treatment strategies for crude oil pipelines with various water cuts and flow conditions.

Accordingly, in an example embodiment, an apparatus to simulate biocide performance in crude pipeline conditions is provided. The apparatus contains three parallel reactors with associated liquid and gas flow systems and electronics, allowing concurrent or simultaneous testing of different biocide application schemes under anoxic conditions. Each reactor includes an agitator (such as a disc rotor), six corrosion coupon holders, an inlet for oil, water, biocide, and nitrogen ($N_2$) gas flow, an outlet at the bottom for water sampling, a height-adjustable dip tube as waste outlet and for oil/water mixed phase sampling, temperature and pressure sensors, a heating band, and a float contact and pressure release valve. The associated systems include liquid and gas containers, pumps, motors, various tubes for liquid and gas flows, biocide addition ports, and sampling points, sufficient to simulate the same or nearly identical crude oil pipeline conditions in all three reactors concurrently (such as simultaneously). The electronics include temperature regulators, frequency inverters, emergency breakers, and computers and software for process control and data acquisition.

The three reactors share enough components (e.g., crude oil and water sources and plumbing) to recreate nearly the same conditions in each reactor. This allows for simultaneously testing the same environmental conditions with as few variations as desired. This also allows for a control reactor to concurrently test for cause and effect relationships. This further allows for multiple identical environments to test for repeatability. In an embodiment, each reactor system has independent control of the oil and water exchange rate as well as the shear rate at the corrosion coupon surface (e.g., bottom of the reactor). Each reactor system also has independent biocide treatment and independent sampling of the water phase (6 o'clock position), the oil/water interface, and the corrosion coupons. The corrosion coupons are small metallic samples (e.g., metal plates or discs) that simulate or resemble a target surface, such as a pipeline wall, for which corrosion information is desired. The coupons can be removed easily and inspected to see if corrosion (or corrosion precursors) are present. Each reactor system further has independent control of the reactor temperature.

In addition to or in place of biocides, in some embodiments, different types of oil field chemicals are concurrently (e.g., simultaneously) tested in the different reactors of the simulation apparatus. For example, in a three-reactor apparatus, a first reactor can be treated with a corrosion inhibitor only, a second reactor can be treated with a biocide only, and a third reactor can be treated with the corrosion inhibitor, followed by the biocide. With this setup, the corrosion inhibitor performance can be evaluated, as can that of the biocide, as can that of the combined treatment, all under otherwise nearly identical conditions.

In an embodiment, the simulation of the pipeline water cut and fluid exchange rate uses two peristaltic pumps delivering oil and water, respectively, at various ratios. In addition, the shear rate in the pipeline is simulated in each reactor by adjusting the rotation speed and the height of the rotor. The apparatus also includes sensors for temperature and pressure monitoring of each reactor. The apparatus, or more specifically each of the reactors, operates autonomously under anoxic conditions while the microorganisms grow in the water phase and colonize the coupon surface. As such, the apparatus requires minimal manual labor, such as only during setup, sampling, exchange of supply fluids, and when de-commissioning an experiment. In an embodiment, the apparatus is cleaned with chemical flushing and sterilized with an in-place autoclave using wet heat.

While much of the present disclosure is directed to the simulation of biocide performance under crude oil pipeline conditions, the present disclosure is not limited to such applications. In other embodiments, the effects of different oil field chemicals, such as corrosion inhibitors, scale inhibitors, or the like, are simulated in the crude oil pipeline conditions.

In an example environment to simulate, a two-phase sweet crude pipeline is used as a model pipeline for the engineering design of an apparatus according to an embodiment. The model pipeline is 129 miles long, using 46 inch and 48 inch pipe to transport sweet crude oil though a desert environment. Usually, the pipeline has low flow velocity, such as less than 0.9 meters per second (m/s). The pipeline is not treated with corrosion inhibitors or biocides. The pipeline has experienced severe internal corrosion due to microbial effects, and has needed extensive repairs. By compiling the pipeline's operating conditions and parameters, the major characteristics of the pipeline can be summarized as: a two-phase system (sweet crude oil and water), with a phase-separated liquid flow, water being at the 6 o'clock (low) position, as well as the corrosion. By using an apparatus according to an embodiment disclosed herein to simulate such a pipeline on a much smaller scale, effective biocide treatment plans can be identified and tested without the inconvenience and cost of using the actual pipeline to conduct such an investigation.

In an embodiment, an apparatus to simulate various crude pipeline conditions with concerns of microbial corrosion is provided to identify pipelines that would benefit from biocide treatment for microbial control. The microbial corrosion in a sweet crude oil pipeline is often caused by water and solids that drop out and accumulate at low spots due to flow conditions such as low flow velocity or stagnant flow. The apparatus provides for simulation of separated oil and water phases, turbulent mixing of oil and water phases, simulation of pipeline shear rates (e.g., pipeline flow velocity changes across different parts of the interior of the pipeline), simulation of water at the 6 o'clock position, and control of the water cut and temperature. The apparatus also provides for up to six commercially available corrosion coupons (e.g., flat discs) in each reactor, coupon removal and replacement during experiments, biofilm growth and biocide treatment, data transfer to computers and storage devices (such as an Excel spreadsheet), and safety features.

In an embodiment, computational fluid dynamics (CFD) simulation and flow calculations are used to evaluate the fluid flow in a model pipeline. By using a range of water cuts and flow velocities in CFD simulations, the dominant flow type under various flow conditions can be determined. By way of example, dimensionless numbers (such as Reynolds, Froude, and Weber numbers) can be used to understand fluid dynamics when scaling down from a pipeline to a laboratory apparatus such as an embodiment. Using conventional equations, the surface shear rate can be calculated to simulate the flow velocity in the pipeline below which biofilm development significantly increases on the surface of the pipeline wall or on the corrosion coupons. CFD simulation and flow calculations can also be used to determine the most important simulation parameters for the apparatus.

The design of the test cell or reactor can factor in these simulation priorities, including: phase separation (e.g., the liquid composition at the coupon surface in the apparatus should match that of the 6 o'clock pipeline position), shear rate at the coupon surface (e.g., should match the 6 o'clock pipeline position, focusing on low flow velocity such as from 0.3 m/s to 1.0 m/s), turbulence magnitude (turbulence (Reynolds number) should match that of the pipeline to maintain interphase mixing, growth potential of cells, and efficacy of biocides), and water cut (lower priority, with CFD simulation showing a phase separation under all relevant pipeline conditions, such as water cut above 3.3% and flow velocity below 1.5 m/s).

In accordance with various embodiments, an apparatus to simulate biocide performance in crude pipeline conditions is provided. The apparatus is configured to simulate two-phase crude pipeline conditions by: simulating separated oil and water phases, simulating flow velocity in the crude pipeline via shear rate simulation, simulating turbulent flow in the crude pipeline, controlling the oil and water ratio, simulating water deposits at the 6 o'clock position, simulating corrosion at the 6 o'clock position, and simulating crude oil pipeline temperatures. The apparatus is further configured to simulate biofilm growth on pipeline surfaces by: allowing biofilm formation and growth on the surface of corrosion coupons at the 6 o'clock position, allowing biofilm formation and growth under anoxic conditions, simulating phase exchange at the oil/water interphase (that provides nutrition for biofilm growth), and simulating the impact of flow velocity and shear rate on biofilm growth.

In addition, the apparatus is configured to evaluate biocide performance and optimize treatment schemes under crude pipeline conditions by: using three parallel reactors for simultaneous testing of different biocide application schemes and treatment optimization; providing biocide treatment to each reactor; providing coupon removal and replacement during experiments; providing sampling of the water, the oil/water interphase, and the corrosion coupons during the experiments; and providing microbial corrosion assessment on the metal coupons.

In an embodiment, a laboratory apparatus is configured to simulate two-phase sweet crude pipeline conditions, develop biofilm on metal coupon surfaces, evaluate biocide performance on such biofilm development, and optimize treatment schemes under the simulated pipeline conditions. Such an apparatus, operating under the simulated crude oil pipeline conditions, improves the biocide evaluation accuracy over water-based systems, shortens field trial durations, accelerates optimization of treatment programs for crude pipelines, and saves the cost of biocide field trials.

Laboratory validation of such an apparatus includes microbial enrichment, validation of biofilm growth, and evaluation of biocide performance. Microbial enrichment includes collecting crude oil and water samples from a model or target pipeline, and formulating an artificial growth media based on the geochemical composition of the model pipeline water, to promote growth of the major corrosion-related bacteria, such as sulfate-reducing bacteria (SRB) and acid-producing bacteria (APB). The microbial enrichment further includes analyzing the model pipeline water and the enrichment culture from this water to determine the number of various microorganisms and the microbial community compositions, to make sure the basic microbial compositions are similar.

In an embodiment, a reactor to simulate biocide performance in crude pipeline conditions is provided. The reactor includes six corrosion coupons and a rotor to generate the required shear to simulate the desired pipeline conditions. Water and crude oil enter the reactor via an inlet, with the water cut being controllable by individual pumps that deliver the fluids. An immersion tube provides an outlet from the reactor. The immersion tube is height adjustable within the reactor to sample, for example, oil, water, or the mixed phase oil and water at the boundary between the two phases. Each coupon is secured with a corresponding coupon holder that uses a ball valve to deploy, retrieve, or exchange coupons during an experiment in the reactor. The rotor speed is controlled by a corresponding shaft and bearings below and outside the reactor.

FIG. 1 is an illustration of an example three-reactor apparatus 100 to simulate biocide performance in crude pipeline conditions, according to an embodiment. Structurally, the apparatus 100 includes an aluminum frame 110 to support the reactors 130 and their corresponding agitator motors 135, and a transparent plastic enclosure 120 (such as plexiglass) to safeguard and isolate the reactors 130 and other equipment (such as for gas containment) while permitting visual observation. The apparatus 100 further includes the three reactors 130 and their corresponding motors 135 (e.g., 3 phase, 380 volt (V) motors). Each reactor 130 includes six corrosion coupons for observing corrosion activity (such as microbial corrosion) together with a rotor for simulating pipeline fluid flow and sensors for determining, for example, temperature and pressure within the reactor 130.

The apparatus 100 further includes various pumps 150 (such as peristaltic pumps) and tubing (such as stainless steel (SS) and flexible) for pumping and delivering liquids and gases such as water, crude oil, $N_2$, and liquid and gas samples and wastes. The apparatus 100 also includes tanks 160 for holding the different liquids used (e.g., input or output) by the reactors, such as water, oil, and waste liquid. In addition, the apparatus 100 includes various electronic equipment 170, such as an electronic panel for displaying simulation data, computers for electronically processing the data, and software for configuring the computers to process the data and make the apparatus 100 function as designed. The electronics can include, for example, one or more custom hardware circuits, programmable logic circuits (PLCs), or computer processors configured with code or other logic to carry out the tasks assigned to the circuits or processors. The electronics can also include a user interface equipped with a touch screen to permit computer interaction.

In further detail, the apparatus 100 includes three parallel reactors 130 (e.g., 12 liters (L) apiece) mounted on an aluminum frame 110 with a plexiglass enclosure 120. An explosive gas sensor and a hydrogen sulfide ($H_2S$) sensor are mounted at the top of the frame 110, inside the plexiglass enclosure 120, and transmit their measurements to a programmable logic controller (PLC, part of the electronics 170). The PLC is configured with code or other programmable logic that causes the PLC to carry out the tasks assigned to it, such as alerting an operator to unsafe or undesired levels of explosive gas or $H_2S$ detected. Each reactor 130 includes a disc rotor, six corrosion coupon holders, an inlet for oil, water, biocide, and $N_2$ gas, an outlet at the bottom for water sampling, a height-adjustable dip tube for use as a waste outlet and for oil/water mixed phase sampling, temperature and pressure sensors, a heating band 140, and a float contact and pressure release valve. The reactor 130 can be cleaned, for example, with a manual chemical scrub, and sterilized by an in-place autoclave with wet heat.

The disc rotor is made of 316 stainless steel (SS), with 300 millimeter (mm) diameter and 8 mm thickness. The disc rotor is electrically insulated from the reactor 130 by a collar made of polytetrafluoroethylene (PTFE, commonly known as Teflon). It is powered by a gear motor 135 with rotation speeds of between 20 and 220 revolutions per minute (RPM or rpm). The motor 135 is controlled using the PLC through a frequency inverter. The height of the disc rotor can be adjusted between 5 mm and 10 mm above the coupons (e.g., 5-10 mm above the bottom of the reactor 130) using the motor 135. The shear rate at the coupon surface is controlled by the rotation speed and the height of the rotor. In addition, each reactor 130 can hold six commercial disc-shaped corrosion coupons with exposed surface area of 1.12 square inches (7.2 square centimeters, or $cm^2$). Each corrosion coupon is made from mild steel (e.g., alloy C1018, from Alabama Specialty Products) and mounted in a polyether-ether-ketone (PEEK) coupon holder for isolation from the metal surface of the reactor base. Each coupon can be removed and replaced during an experimental run and with minimal disruption to any experiment in progress.

The electronics panel, computer, and software 170 (collectively known as "electronics 170) includes the PLC configured with code (or other programmable logic) to carry out process control and data acquisition. The PLC is further configured (e.g., with code or other programmable logic) to frequently (such as continuously) read data from the temperature regulators, the pressure sensors, and the gas sensors. The PLC is also configured to control the pumps and the frequency inverters. The electronics 170 can also include a computing device (such as a laptop, a workstation, a tablet, a smartphone, part of a server, or a dedicated hardware circuit, as in an FPGA or ASIC, or the like). The instrumentation data obtained by the apparatus 100 can be stored or recorded in a non-transitory storage device, such as a disk drive or solid state storage device, such as a network-accessible storage device attached to a wired or wireless network. The electronics 170 further includes one or more temperature regulators each configured to read the reactor temperature through the temperature sensors and adjust the temperature through the heating bands 140. The electronics 170 also includes one or more frequency inverters each configured to set the rotation speed of the motors 135, allowing the motors 135 to run between 20 rpm and 220 rpm.

In addition, the electronics 170 includes an emergency breaker that is configured to work with an emergency button to stop all hazardous parts in case of an emergency. For example, in an embodiment, the emergency breaker, once engaged (such as by pushing the emergency button), is configured to force the motors, pumps, and heating for the apparatus 100 to stop. The electronics 170 further includes a computer configured by code to perform as the primary user interface, connected to the PLC via an Ethernet cable. By way of example, the computer can be configured by code to run a LabVIEW software application customized for the apparatus 100. The LabVIEW customization can include code that configures the computer to control various parameters frequently (such as continuously) when running the apparatus 100, such as the oil and water mix ratio, the shear rate, and the reactor temperature. The customization can further include code to provide step-by-step guides for manual handling and maintenance of the apparatus 100, such as liquid container changes, biocide addition, sample collection, cleaning, and sterilization.

The software can include further instructions that when executed by the computer, cause the computer to control parameters such as rotation speed of the rotor, test cell temperature, and fluid exchange rate. The software can also configure the computer to assist users with when and how to perform maintenance (e.g., tank changes, removal and insertion of coupons, extraction of water samples, addition of biocide, and the like). By way of example, the software can configure the computer to receive input from and direct output to a touch screen configured to operate as a control center for the apparatus 100.

The customization can also include code that configures the computer to perform data logging and output: By way of example, the software can include code that configures the computer to log relevant information about an experimental run (e.g., rotor rotation speed, reactor temperature, reactor pressure, oil/water liquid flow rates, remaining liquid volume; date, time, and type of manual operations; and results of sample analyses), to save data in transition-minimized differential signaling (TDMS) format, and to export data to an electronic spreadsheet (such as an Excel workbook). In addition, the customization can configure the computer to calculate the shear rate based on pipeline conditions, and to determine a rotor rotation speed to match the pipeline shear rate.

Figure 2:
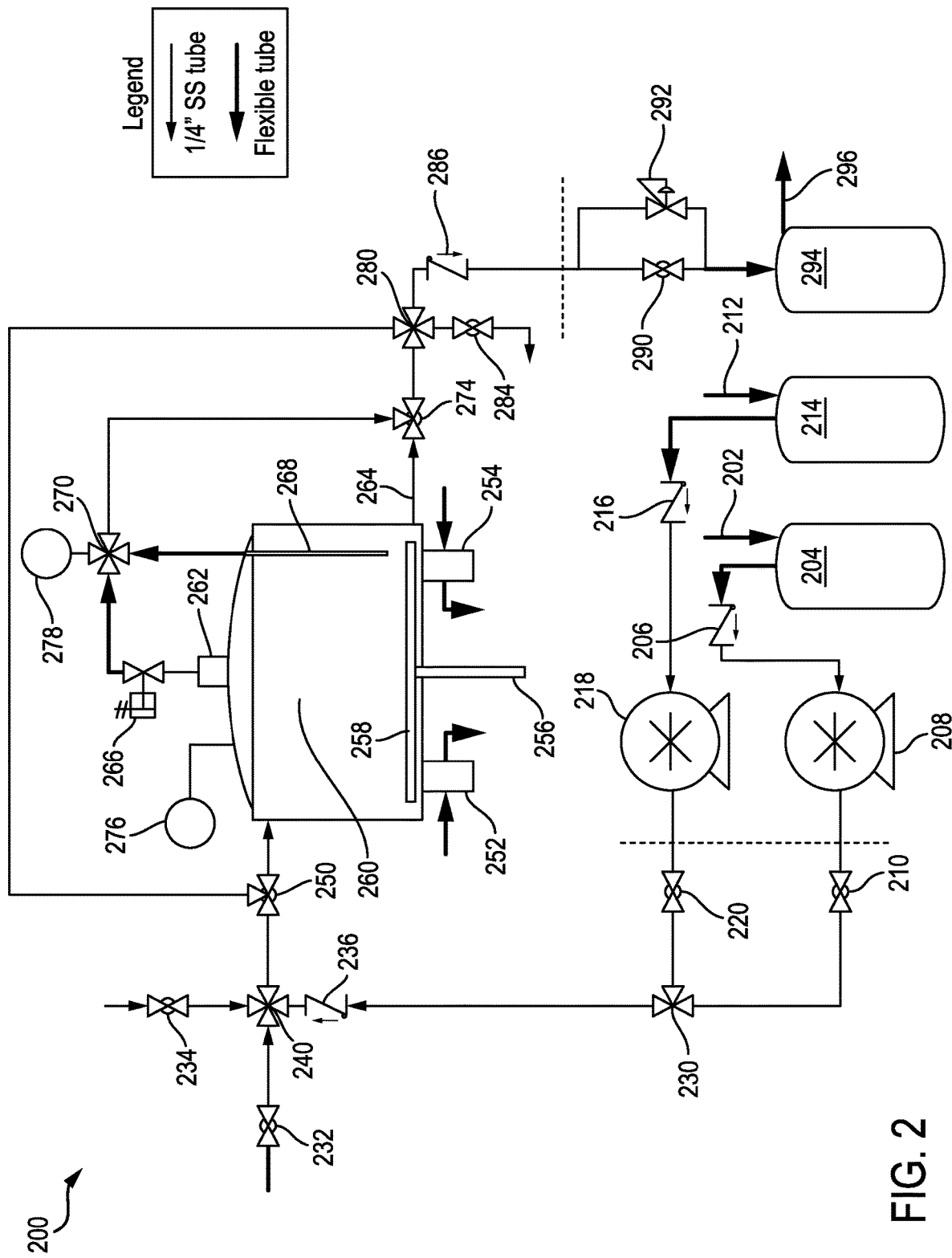
FIG. 2 is a schematic diagram of an example liquid and gas flow for an apparatus to simulate biocide performance in crude pipeline conditions, according to an embodiment.

FIG. 2 is a schematic diagram of an example liquid and gas flow for an apparatus 200 to simulate biocide performance in crude pipeline conditions, according to an embodiment. The apparatus 200 includes three reactors (including reactor 260) for simulating the crude oil pipeline. Each reactor 260 includes a rotor 258 for simulating the crude pipeline flow conditions in the reactor 260. The rotor 258 is driven by a shaft 256 connected to a motor for controlling the rotation speed of the rotor. The apparatus 200 also includes both SS tubes (e.g., ¼ inch SS tube) and flexible tubing to route the various fluids (liquids and gases) between the different components throughout. The liquid containers include an oil tank 204, a water tank 214, and a waste tank 294 (for example, Thielmann SS pressure vessels can be used for these tanks). Each such tank is also equipped with a built-in pressure relief valve and a gas inlet for pressure equalization. Within the reactor 260, liquid can be drawn from the bottom of a height-adjustable dip tube 268 (e.g., to obtain a sample of an oil/water mixture at the boundary of the oil and water phases in the reactor 260).

Two peristaltic pumps (such as with three channels each, one channel for each reactor 260), including oil pump 208 and water pump 218, deliver oil and water at various ratios to the three reactors (e.g., using oil valve 210, water valve 220, and mixing valve 230, for eventual delivery to an inlet valve 250 and reactor 260 via mixing valve 240). The inlet valve 250 also serves as a bypass valve to divert any inputs from the reactor 260. Check valves, such as check valve 206 between the oil tank 204 and oil pump 208, check valve 216 between the water tank 214 and water pump 218, and check valve 236 between the mixing valve 230 and mixing valve 240, can be used to prevent unintended backflow along the liquid paths. The pump rate at each pump can be adjusted, for example, between 0.013 milliliters per minute (ml/min) and 12.7 ml/min for 1.52 mm tubing. Various tubing materials can be used in the apparatus 200, such as SS, PTFE, and Viton tubes. SS tubing can be mainly for liquid flow, PTFE for gas flow, and Viton for the flexible connections of the main system, as one example of implementing a particular embodiment. The tubes can be cleaned and sterilized, for example, by chemical flushing.

$N_2$ gas flow is used for a variety of purposes, such as providing anoxic conditions for the simulation. $N_2$ gas flows 202 and 212 to the oil tank 204 and water tank 214, respectively, equalize pressure in the tanks while providing anoxic conditions. Further, $N_2$ gas flow 232 is provided to the inlet valve 250 (via mixing valve 240) to help drain the reactor 260 during cleaning and maintenance. In addition, $N_2$ gas flows are supplied to corresponding coupon holder ball valves 252 and 254 of the reactor 260 to prevent an air ingress to the reactor 260 and limit the spill of fluid during coupon insertion, removal, and replacement. The coupons are at the top of the coupon holders 252 and 254, flush with the bottom inside surface of the reactor and below the rotor 258, and removable/replaceable via the corresponding ball valves with minimal disruption of the experiment in the reactor 260.

Biocide can be added to the mixed phase liquid at the mixing valve 240 (via biocide inlet 234) immediately before the mixture enters the reactor 260. For example, the biocide inlet 234 can be a syringe with a Luer-lock (or Luer taper) connection. The check valve 236 (one-way valve) ensures that the biocide only flows towards the reactor 260, not backwards toward the liquid supplies. The biocide (or other oil field chemical, such as corrosion inhibitor or scale inhibitor) can be delivered independently and distinctly for each reactor 260 (e.g., via dedicated biocide inlets 234). The reactor 260 further includes a float contact 262 and pressure release valve 266 for releasing excess pressure in the reactor 260. The output of the float valve 266 is directed to a mixing valve 270 that also receives the output of the dip tube 268.

In addition, the reactor 260 includes a temperature sensor 276 and a pressure sensor 278 that measure (such as periodically) the temperature and pressure of the inside of the reactor 260. This can help ensure that the desired environmental conditions (or ranges) for the simulation are maintained throughout the experiment. For example, the temperature sensor 276 can mount to a lid of the reactor 260 to monitor the temperature of the reactor 260 while the pressure sensor 278 can mount to the top of the dip tube 268 to monitor the pressure of the reactor 260 from the mixing valve 270.

The reactor 260 includes a water port 264 for sampling the water phase (bottom, corresponding to the 6 o'clock position of the pipeline being simulated) of the reactor 260. The water port 264 combines with an output of the mixing valve 270 at an outlet valve 274. The output of the outlet valve 274 combines with the output of the bypass valve 250 (for fluid diverted from entering the reactor 260). After the outlet lines of the reactor 260 have combined to one at the mixing valve 280, there is a liquid sampling point 284. The sample point 284 allows the operator or automated collection (e.g., under control of a processor configured by code to manage the collection) to collect samples from the reactor 260. For instance, the samples can come from the water phase (from the bottom of the reactor 260) or the oil/water mixed phase (from the height-adjustable dip tube 268 inside the reactor 260).

The mixing valve 280 can further divert output fluid from the reactor 260 to the waste tank 294 via a waste valve 290. A check valve 286 is used to prevent backflow from the waste tank 294 to the mixing valve 280 (and other components, such as the reactor 260 or sample point 284). A safety valve 292 can act as a fail-safe should preset or predetermined pressure or temperature levels of the waste fluids be exceeded. An exhaust vent 296 is provided to remove any (excess) gas entering the waste tank 294.

Figure 3:
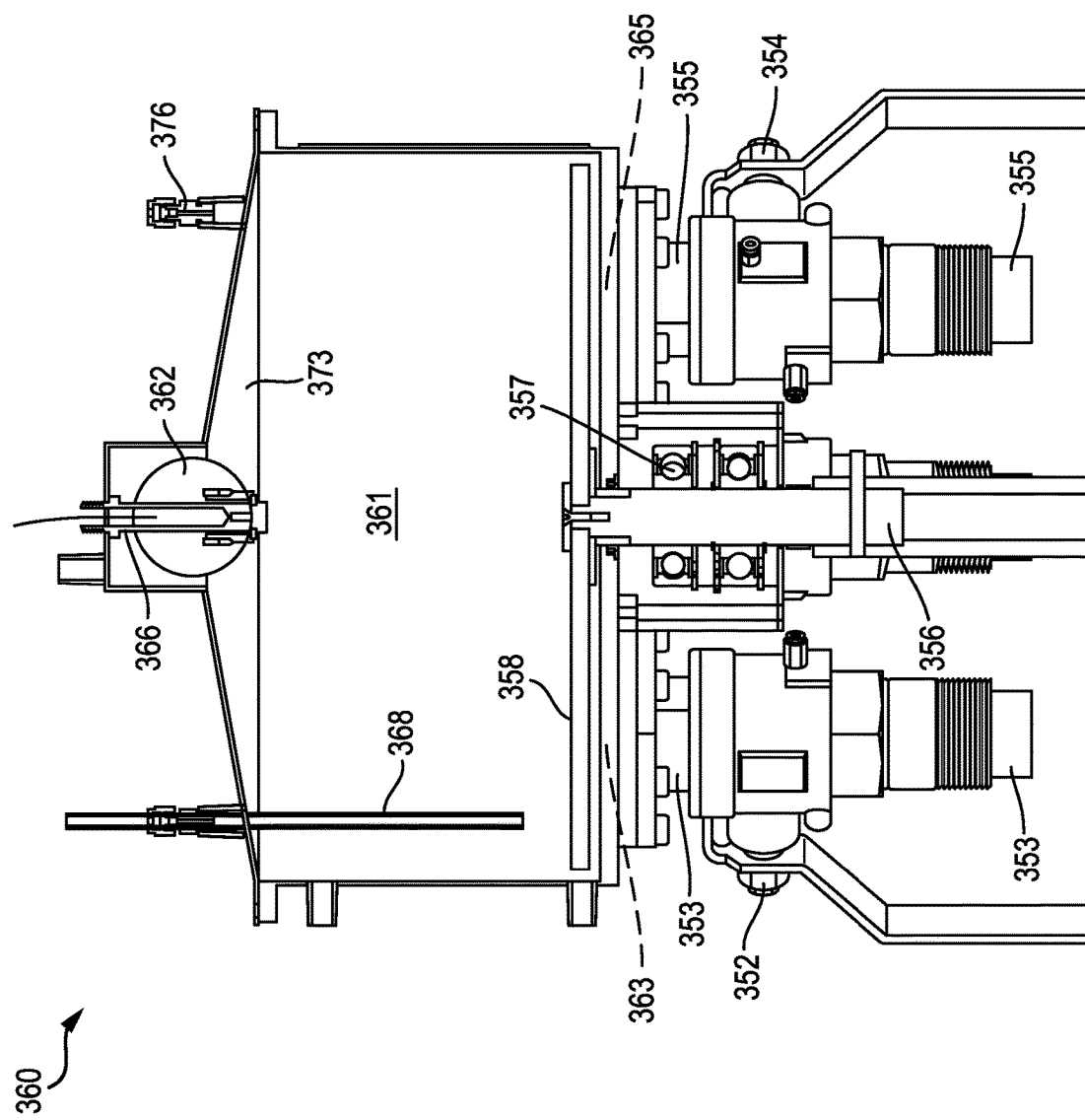
FIG. 3 is a cutaway view of an example reactor to simulate biocide performance in crude pipeline conditions, according to an embodiment.

FIG. 3 is a cutaway view of an example reactor 360 to simulate biocide performance in crude pipeline conditions, according to an embodiment. The reactor 360 includes a bucket 361 with a lid 373 to contain the two-phase oil and water combination that simulates the crude pipeline. The reactor 360 further includes six coupons (such as corrosion coupons 363 and 365) at the bottom of the bucket 361 secured by corresponding coupon holders (such as coupon holders 353 and 355, respectively). Each coupon holder 353 or 355 in FIG. 3 is designated with two lines, one for a lower portion of the coupon holder and one for an upper portion of the coupon holder. The coupon holders 353 and 355 allow for retrieval of the respective coupons 363 and 365 during an experiment using corresponding ball valves 352 and 354, as illustrated in more detail in FIGS. 4A-4B. To this end, corresponding $N_2$ gas flows are supplied to the ball valves 352 and 354 to, for example, prevent air ingress to the reactor 360 and limit spills during removal and replacement of the coupons 363 and 365 using the ball valves 352 and 354, respectively.

The reactor 360 further includes a rotor 358 connected to a shaft 356 that is connected to bearings 357 (e.g., to stabilize and improve performance of the shaft 356) and a motor for rotating the rotor 358 using the shaft 356 and the bearings 357. The rotor 358 simulates the pipeline flow conditions in the bucket 361. The rotor 358 is at the bottom of the bucket 361, above the coupons 363 and 365. The reactor 360 further includes a dip tube 368 for sampling the oil and water at the phase boundary between the two phases. In addition, the reactor 360 includes a float contact 362 coupled to a float valve 366 at the top of the reactor 360. The float contact 362 includes a hollow SS ball that floats on the interface between oil and gas (at the top of the reactor 360). The float contact 362 is mounted at the top of the lid 373. When the gas amount in the reactor 360 increases, the ball lowers, and the float valve 366 opens to reduce the gas headspace in the reactor 360. The reactor 360 further includes a temperature sensor 376 mounted to the lid 373 to monitor the temperature inside the reactor 360.

Figure 4A:
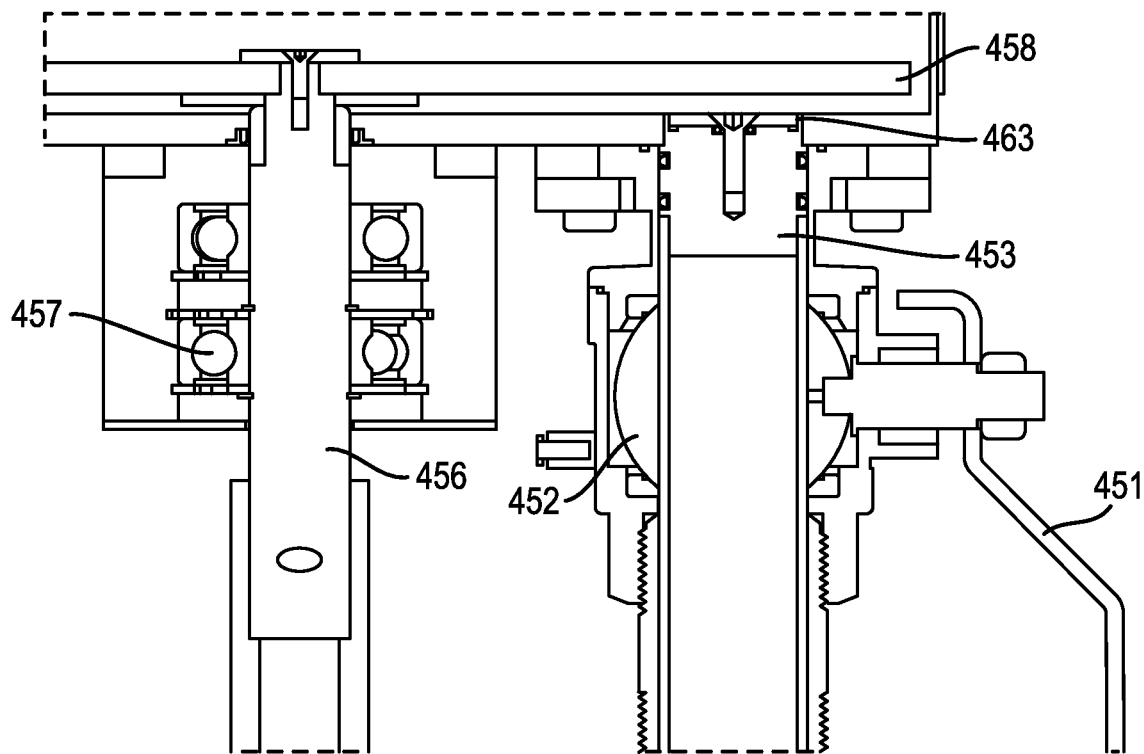
FIGS. 4A-4B are cutaway views of a reactor, such as the reactor of FIG. 3, illustrating an example coupon holder and ball valve before and after retrieval of a corrosion coupon from the bottom of the reactor, according to an embodiment.
Figure 4B:
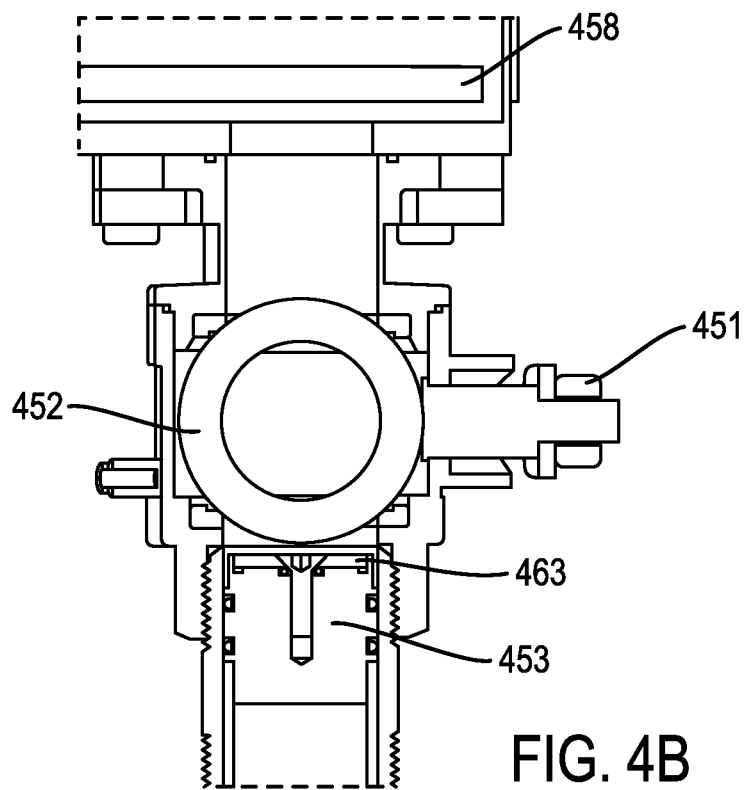

FIGS. 4A-4B are cutaway views of a reactor, such as the reactor 360 of FIG. 3, illustrating an example coupon holder 453 and ball valve 452 before and after retrieval of a corrosion coupon 463 from the bottom of the reactor, according to an embodiment. Many of the components of the reactor of FIGS. 4A-4B are similar to the reactor 360 of FIG. 3, such as rotor 458, bearings 457, and steel axle (shaft) 456. FIG. 4A illustrates the corrosion coupon 463 flush mounted to the bottom of the reactor. The coupon 463 is at the top of and secured to the coupon holder 453 (such as by a center-mount screw). The coupon holder 453 is long, extending through the ball valve 452 (in the open position, as indicated by the parallel orientation of the ball valve handle 451 with respect to the coupon holder 453), and includes O-rings below the coupon 463 to form a watertight seal with the reactor.

FIG. 4B, on the other hand, illustrates the corrosion coupon 463 after retrieval from the reactor, with the ball valve 452 in the closed position, as indicated by the perpendicular orientation of the ball valve handle 451 with respect to the coupon holder 453. The closed ball valve 452 seals the reactor, permitting complete removal of the coupon holder 453 and access to the coupon 463 with minimal liquid loss from the reactor in the process. $N_2$ gas is further directed to the ball valve 452 to minimize the risk of air (oxygen) ingress to the reactor during the coupon removal and replacement process. The coupon 463 can be analyzed for corrosion-related effects such as biofilm presence, weight loss, pitting, or other metallurgical phenomena indicative of corrosion. Further, a replacement coupon 463 can be flush mounted to the bottom of the reactor by attaching the replacement coupon 463 to the coupon holder 453 (e.g., with a center-mount screw) and reversing the retrieval process.

Figure 5:
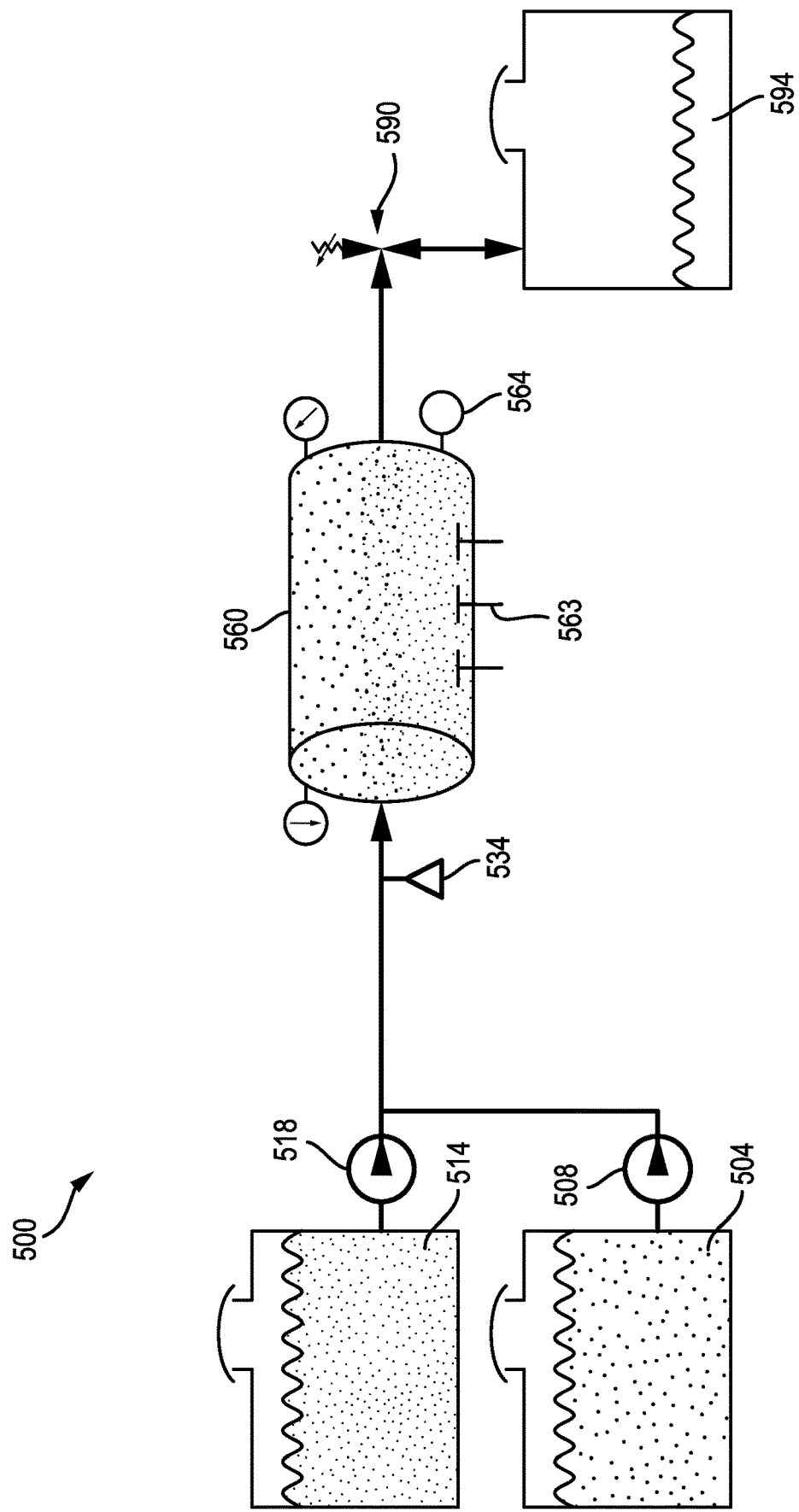
FIG. 5 is a schematic diagram of an example apparatus to simulate biocide performance in crude pipeline conditions, according to another embodiment.

FIG. 5 is a schematic diagram of an example apparatus 500 to simulate biocide performance in crude pipeline conditions, according to another embodiment. The apparatus 500 includes three main parts: liquid and gas flow (including containers, piping, and pumps), test cells/reactors (including coupon holders, fluid injection ports, and sampling points), and electronics (including computer and software). The software contains computer instructions that when executed on the computer, cause the computer to control the apparatus 500 and acquire data from different instrumentation devices of the apparatus 500. In an embodiment, the apparatus 500 includes three parallel test cells for simultaneous testing of multiple biocide treatments. However, the present invention is not limited thereto, and in other embodiments, different numbers of parallel test cells are present, such as four or two.

In further detail, the apparatus 500 includes storage containers 504, 514, and 594 for crude oil, water, and waste liquid, respectively, to manage the liquid input and output for the apparatus 500. The apparatus 500 further includes oil pump 508 and water pump 518 (such as peristaltic pumps) to deliver the crude oil and water from the oil and water containers 504 and 514, respectively, to the reactors. The apparatus 500 also includes biocide injection ports 534 for supplying biocide (or other oil field chemical, such as a corrosion inhibitor or scale inhibitor) to the corresponding reactors.

Considering only a single reactor for ease of description, the apparatus further includes a test cell (or reactor) 560 for simulating the two-phase crude pipeline. The test cell 560 includes corrosion coupons 563 for testing the water phase (e.g., the lower or water portion) of the test cell 560 for symptoms indicative of pipeline corrosion (e.g., microbial corrosion such as biofilm-induced corrosion). The test cell 560 further includes a fluid sample retrieval port 564 for sampling the water phase of the liquid in the test cell 560, such as to test for biofilm, conditions that serve as precursors to biofilm, effects of biocide treatment, or to test for similarity of the water phase in the test cell 560 versus that of the crude pipeline being simulated. The apparatus 500 also includes a waste valve 590 for eliminating waste fluids (e.g., undesired, unnecessary, or excess liquids or gases) from the test cell 560 to the waste container 594.

In an embodiment, each of the test cells 560 has the following capabilities: oil/water separation (e.g., two-phase liquid portion, with water at the 6 o'clock position and oil at the 12 o'clock position), control of the shear rate (e.g., the velocity gradient as measured across the diameter of the fluid-flow channel, or in this case, within the test cell 560), control of the mixing of oil and water at the interphase of the two-phase system, and control of the water cut (e.g., ratio of water to oil or of water to the total liquid).

Figure 6B:
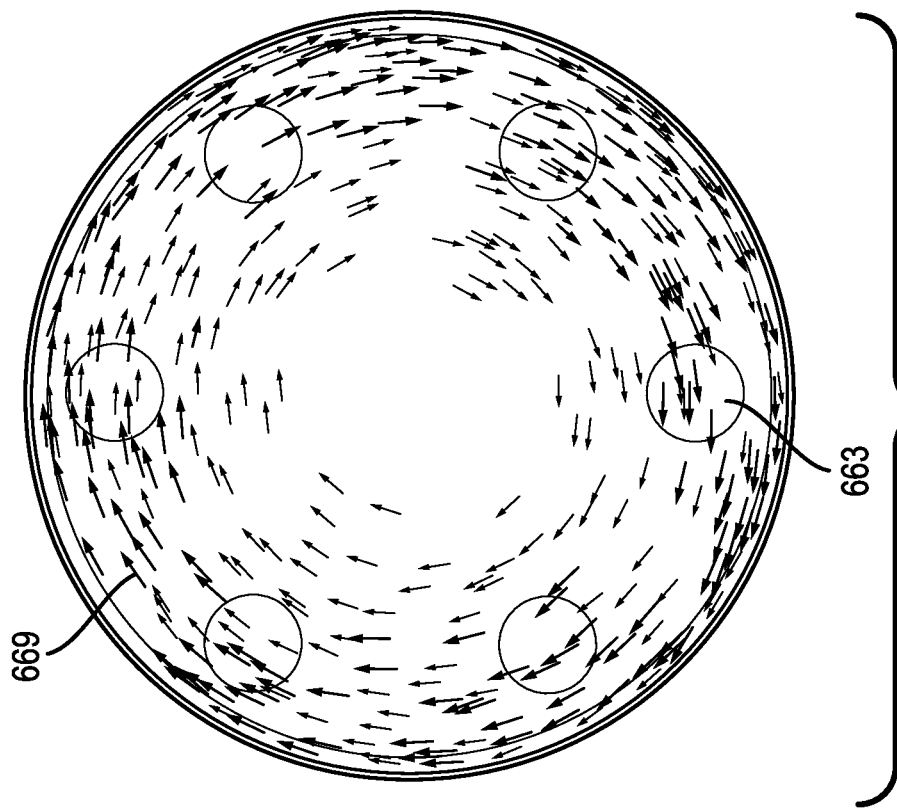
FIGS. 6A-6B are cutaway views of an example reactor to simulate biocide performance in crude pipeline conditions, according to another embodiment.
Figure 6A:
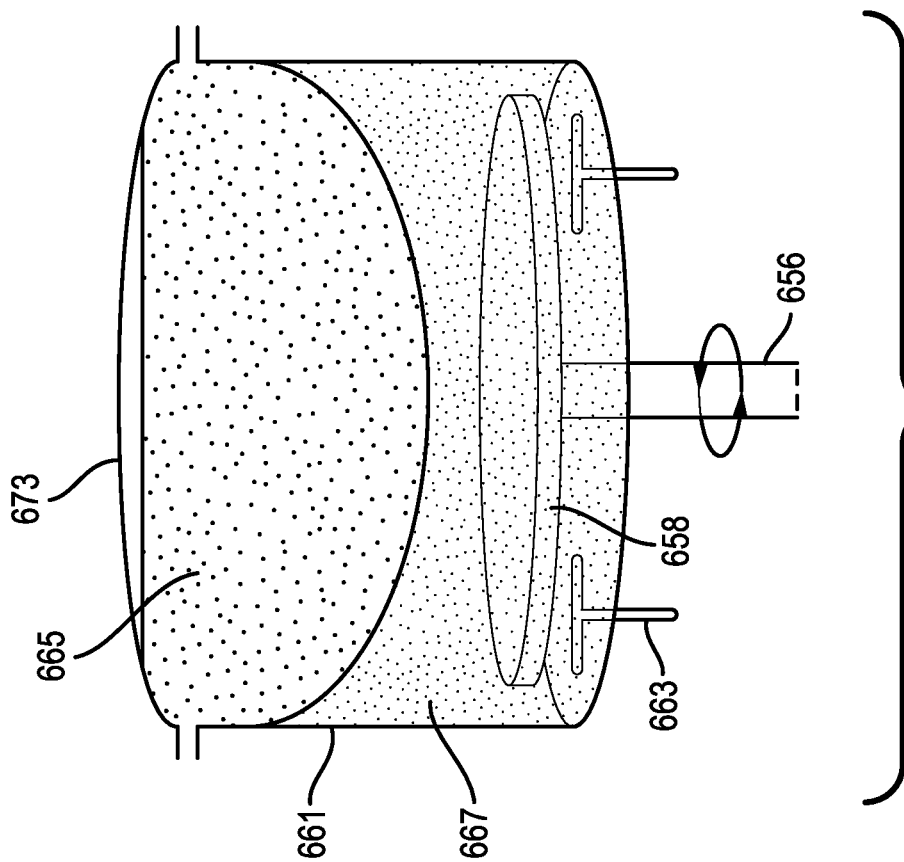

FIGS. 6A-6B are cutaway views (side and bottom, respectively) of an example reactor to simulate biocide performance in crude pipeline conditions, according to another embodiment. There are many possible designs of such reactors and their corresponding agitators. However, the design in FIGS. 6A-6B (including a closed bucket with a disc rotor and bottom corrosion coupons) is used throughout as an example reactor design that has overall characteristics that compare favorably to other similar or comparable designs. These characteristics include good phase separation of the oil and water, good control of the shear rate at the coupons, good control of oil and water interaction at the interphase, and good cleaning and sterilization properties. In addition, the example reactor design has other desirable qualities, such as a manageable amount of liquid to simulate the crude pipeline (e.g., using the closed bucket as opposed to a more pipeline-like design such as a closed flow loop) as well as the ability to use standard commercial corrosion coupons (instead of custom-shaped coupons).

In further detail, the reactor design of FIGS. 6A-6B includes a bucket 661 closed with a lid 673 to produce a sealed system having a few access ports as described throughout. The bucket 661 holds a sample of crude oil 665 and water 667 sufficient to simulate the conditions of a crude pipeline whose corrosion (such as microbial corrosion) treatment is being investigated. In addition, the reactor design includes a rotor 658 near the bottom of the bucket 661 that rotates (as controlled by a shaft 656 coupled to a motor). The rotor rotation rate can be varied, such as between 20 rpm and 220 rpm, to better simulate the flow conditions within the crude pipeline. The rotor height can also be adjusted (such as within the water phase) to better simulate desired crude pipeline conditions.

The flow velocity is modeled using a CFD simulation and illustrated schematically in FIG. 6B, where the direction, size, and transparency of the arrows 669 indicates the direction and speed of the corresponding flow at that location. The larger, darker arrows near the perimeter indicate a relatively strong (clockwise) flow of water, as opposed to the smaller, fainter arrows closer to the center, which indicate a relatively weak (but still clockwise) flow of water. Accordingly, during the simulation, the water at the sides of the bucket 661 reaches a higher height compared to that at the center of the bucket 661.

Also illustrated in FIGS. 6A-6B are six corrosion coupons 663 flush with the bottom of the inside of the bucket 661. The coupons 663 are configured to be deployable and removable during a simulation with little or minimal impact to the simulation (such as through coupon holders illustrated and discussed elsewhere). Since the extent and the rate of corrosive activity is relatively slow and tracked over time, six coupons 663 provides a sufficient number of sample points to get reliable data over time, permitting testing of one or two points at a time while other regions continue to be subjected to the simulation.

In the reactor design of FIGS. 6A-6B, the shear rate at the coupon surface (e.g., bottom of the bucket 661) can be adjusted using the rotation speed and height of the disc rotor 658. The horizontal disc rotor 658 facilitates phase separation and oil/water mixing. Six commercially available, flat disc coupons 663 are flush mounted at the bottom of the test cell.

Figure 7:
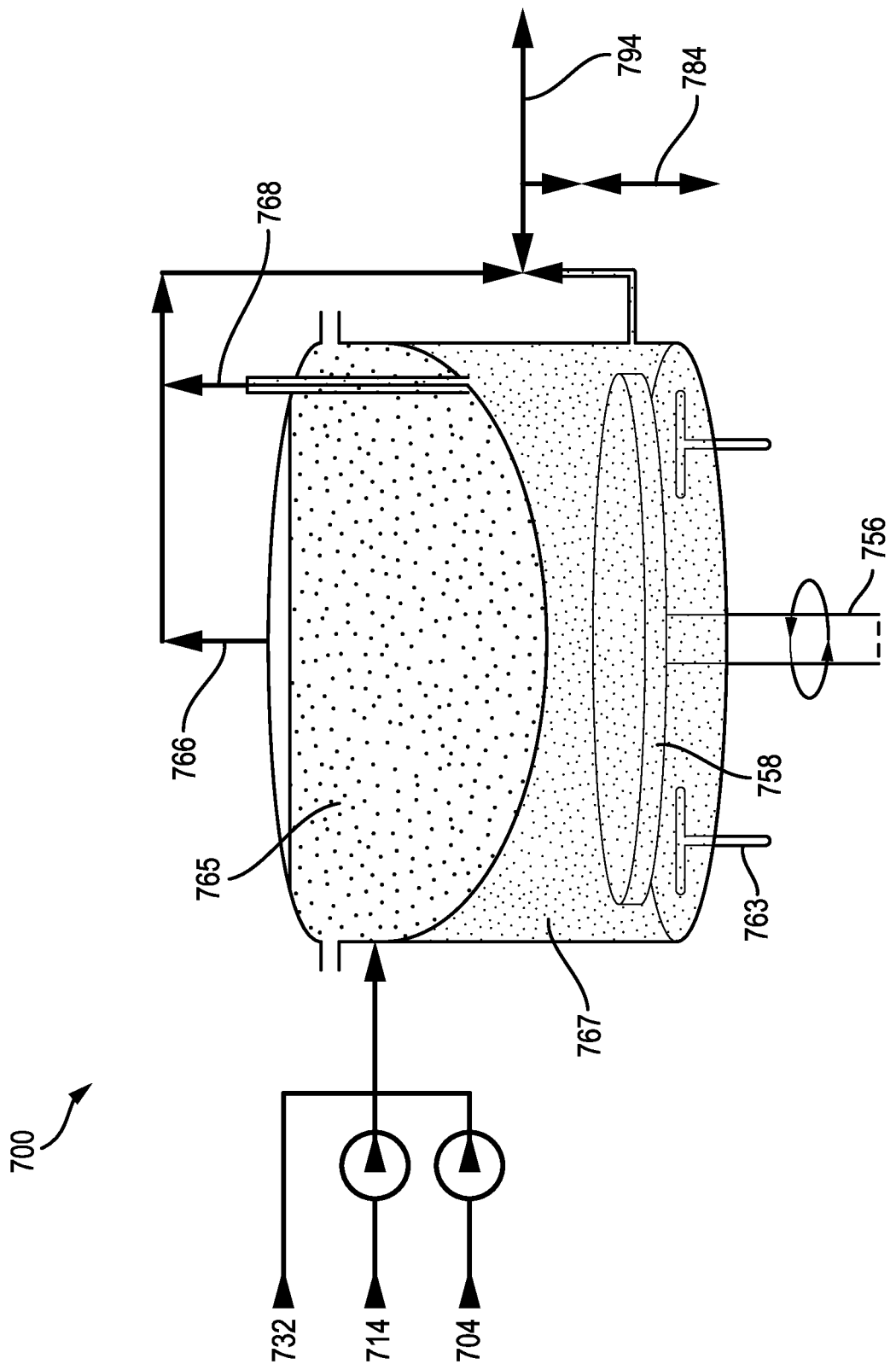
FIG. 7 is a schematic diagram of an example apparatus to simulate biocide performance in crude pipeline conditions, according to another embodiment.

FIG. 7 is a schematic diagram of an example apparatus 700 to simulate biocide performance in crude pipeline conditions, according to another embodiment. The apparatus design of FIG. 7 has some features worth noting. The apparatus 700 uses a bucket test cell/reactor having a disc rotor 758 (driven by a shaft 756) and bottom coupons 763. The apparatus 700 further uses several such test cells, such as three. For example, three nearly identical reactors sharing as many common components as possible provides for simultaneous testing of different biocide application schemes under close to identical conditions. It should be noted that using fewer such test cells makes such simultaneous testing limited or impossible, while using more than three complicates the design of the apparatus 700 while only providing marginal added simultaneous testing capability. Nonetheless, in other embodiments, different numbers of test cells, such as four, five, or even two are provided.

In FIG. 7, a single reactor is illustrated. Through the use of electronics, such as a computer programmed with code to carry out its functions, the user can control simulation parameters such as the oil and water flow rate (e.g., through oil supply flow 704 and water supply flow 714), the rotation speed of the rotor 758 (corresponding to the pipeline flow velocity), and the fluid composition (water cut or proportion of water 767 to oil 765) in the reactors. Nitrogen ($N_2$) flow 732 is used to ensure anoxic conditions in the system. A sample point 784 is located downstream of the reactor for sampling and analysis of the water phase (e.g., from a bottom port) or the oil/water mixed phase 768 (e.g., from a dip tube adjusted to the height of the interphase of the oil 765 and water 767). Undesired gas 766 is vented from the test cell. Undesired fluids are directed to a waste flow 794 (e.g., for eventual collection and disposal).

The apparatus 700 has some key features: three experiments can be conducted in parallel using nearly identical configurations (except for variables being tested), the oil and water exchange rate can be controlled separately for each reactor (such as by using two corresponding peristaltic pumps for the oil and water, respectively), and the oil and water phases in the test cell stay separated (as they are in a crude pipeline being simulated). Further features include: the ability to simulate turbulent mixing of the oil and water phases, the ability to control the shear rate at the coupon surface separately for each reactor (such as by the rotation speed and height of the rotor), the ability to allow biofilm development on the coupon surface and to direct biocide treatments to these surfaces, the ability to add biocide separately to each reactor using syringes with Luer-lock connections, and the ability to sample liquid phases separately for each reactor (e.g., through a fixed water sampling port and an adjustable dip tube for oil/water interface sampling).

Still further features include: the ability to install and replace corrosion coupons during experiments with minimal disruption to an ongoing experiment, the ability to maintain a sterilized setup (e.g., by chemical flushing and an in-place autoclave), the ability to operate under anoxic conditions (e.g., by $N_2$ flushing), and the ability to control reactor temperature (e.g., by using a heating band together with a temperature regulator).

Figure 8:
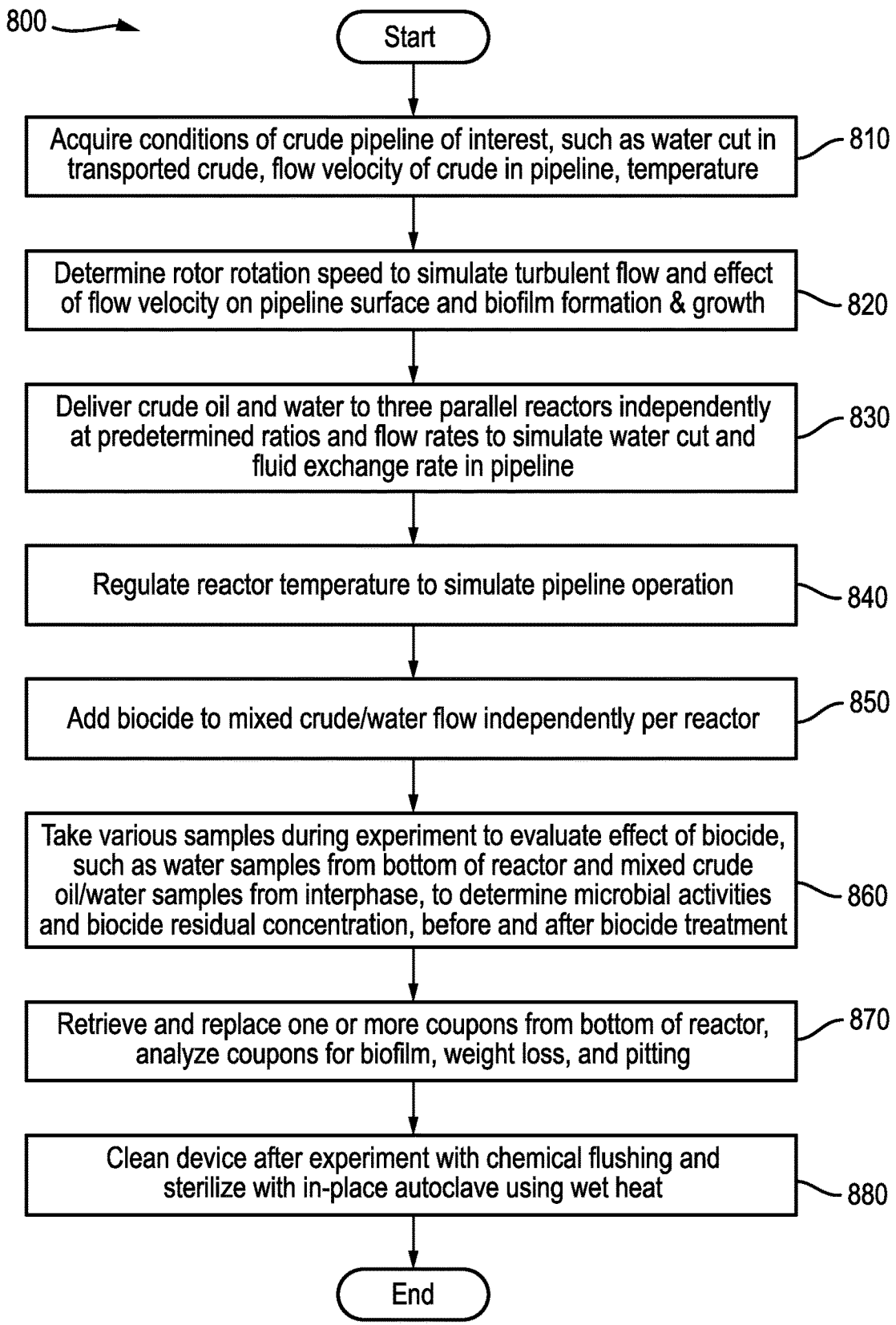
FIG. 8 is a flow chart of an example method to simulate and evaluate biocide performance in crude pipeline conditions, according to an embodiment.

FIG. 8 is a flow chart of an example method 800 to simulate and evaluate biocide performance in crude pipeline conditions, according to an embodiment. Portions of this and other methods disclosed herein can be performed on a custom or preprogrammed logic device, circuit, or processor, such as the PLC, computer, software, and other electronics 170 of FIG. 1. The device, circuit, or processor can be, for example, a dedicated hardware device or computer server, or a portion of a server or computer system. The device, circuit, or processor can include a non-transitory computer readable medium (CRM, such as read-only memory (ROM), flash drive, or disk drive) storing instructions that, when executed on one or more processors, cause portions of the method 800 (or other disclosed method) to be carried out. It should be noted that in other embodiments, the order of the operations can be varied, and that some of the operations can be omitted.

In the example method 800, experiments are designed to evaluate and optimize the biocide performance under the simulated crude pipeline conditions. The method 800 can be performed, for example, using crude pipeline simulation apparatus 200. In the method 800, processing begins with acquiring 810 the conditions and characteristics of the crude oil pipeline of interest, such as the water cut in the transported crude oil, the flow velocity of the crude oil in the pipeline, temperature, and the like. Of particular interest are the pipeline characteristics that affect the production of biofilm and other sources of microbial corrosion.

The method 800 further includes determining 820 (such as with a PLC or computer processor) the rotor rotation speed of a reactor (such as rotor 258 in reactor 260) in order to simulate turbulent flow and the effect of flow velocity on the pipeline inner surface. The rotor rotation speed can be calculated, for example, using a flow calculator application incorporated in a LabVIEW software application customized by code to calculate the corresponding rotor rotation speed from the desired flow velocity. The flow velocity on the pipeline inner surface further affects the biofilm formation and growth, which are key indicators and precursors to microbial corrosion. The flow velocity on the pipeline inner surface is also expressed as the shear rate on the coupon surface of the simulator, which equates to the 6 o'clock position of the pipeline.

The method 800 also includes delivering 830 water and crude oil to three parallel reactors independently and at predetermined ratios and flow rates to simulate the water cut and fluid exchange rate in the pipeline. By way of example, the simulation apparatus includes two peristaltic pumps (such as oil pump 208 and water pump 218), one for crude oil and one for water. Each pump has three channels, one for each reactor in the three-reactor simulation apparatus. The two pumps are programmable to deliver the desired water and crude oil ratio and flow rates, as controlled by an electronic circuit such as the PLC or computer processor configured with code. In addition, the method 800 includes regulating 840 the temperature of the reactors to simulate the pipeline operation temperature. This can be accomplished, for example, by the PLC activating a heating band that heats the reactor in response to a temperature sensor indicating the reactor is below the desired temperature to simulate the pipeline operation.

The method 800 further includes adding 850 biocide to the mixed crude oil/water flow independently for each reactor. By way of example, the biocide can be added through a dedicated biocide inlet (such as biocide inlet 234) for each reactor. In this fashion, different treatment regimens can be applied, such as different injection dosages, durations, and frequencies in order to evaluate the biocide performance or optimize the treatment regimens. The method 800 also includes obtaining 860 various samples (such as through water sampling port 264 and dip tube 268) during the experiment to evaluate the effect of the biocide. For example, the samples can include water samples from the bottom of the reactor and mixed crude oil/water samples from the interphase region of the crude oil and water. The water samples can be obtained, for instance, from a water sample port at the bottom of the reactor while the mixed crude oil/water samples can be obtained through a height-adjustable dip tube. The samples can be used, for example, to determine microbial activities and biocide residual concentration, before and after the biocide treatment.

In addition, the method 800 includes retrieving 870 one or more corrosion coupons from the bottom of the reactor. By way of example, each reactor can include six commercially available, flat disc corrosion coupons (such as corrosion coupon 463) that are flush mounted to the bottom of the reactor. The coupons are individually retrievable and replaceable from the reactor during and after an experiment. The coupons can be retrieved from the reactor, for instance, for biofilm analysis, weight loss analysis, pitting analysis, and other metallurgical analyses. Further, new corrosion coupons can be inserted during the experiment to replace any retrieved coupons. This can be accomplished, for example, through special design of a corrosion coupon holder (such as corrosion holder 453) to minimize oil spill and avoid oxygen ingress during the coupon replacement. The method 800 further includes cleaning 880 the device after an experiment, using chemical flushing and sterilization with an in-place autoclave applying wet heat. This is an important feature that should be part of any microbiology work to eliminate carry-over contamination from one experiment to the next.

The methods described herein may be performed in part or in full by software or firmware in machine readable form on a tangible (e.g., non-transitory) storage medium. For example, the software or firmware may be in the form of a computer program including computer program code adapted to perform some or all of the steps of any of the methods described herein when the program is run on a computer or suitable hardware device (e.g., FPGA), and where the computer program may be embodied on a computer readable medium. Examples of tangible storage media include computer storage devices having computer-readable media such as disks, thumb drives, flash memory, and the like, and do not include propagated signals. Propagated signals may be present in a tangible storage media, but propagated signals by themselves are not examples of tangible storage media. The software can be suitable for execution on a parallel processor or a serial processor such that the method steps may be carried out in any suitable order, or simultaneously.

It is to be further understood that like or similar numerals in the drawings represent like or similar elements through the several figures, and that not all components or steps described and illustrated with reference to the figures are required for all embodiments or arrangements.

The terminology used herein is for the purpose of describing particular embodiments only and is not intended to be limiting of the invention. As used herein, the singular forms "a," "an," and "the" are intended to include the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof.

Terms of orientation are used herein merely for purposes of convention and referencing, and are not to be construed as limiting. However, it is recognized these terms could be used with reference to a viewer. Accordingly, no limitations are implied or to be inferred. In addition, the use of ordinal numbers (e.g., first, second, third) is for distinction and not counting. For example, the use of "third" does not imply there is a corresponding "first" or "second." Also, the phraseology and terminology used herein is for the purpose of description and should not be regarded as limiting. The use of "including," "comprising," "having," "containing," "involving," and variations thereof herein, is meant to encompass the items listed thereafter and equivalents thereof as well as additional items.

While the disclosure has described several exemplary embodiments, it will be understood by those skilled in the art that various changes may be made, and equivalents may be substituted for elements thereof, without departing from the spirit and scope of the invention. In addition, many modifications will be appreciated by those skilled in the art to adapt a particular instrument, situation, or material to embodiments of the disclosure without departing from the essential scope thereof. Therefore, it is intended that the invention not be limited to the particular embodiments disclosed, or to the best mode contemplated for carrying out this invention, but that the invention will include all embodiments falling within the scope of the appended claims.

What is claimed is:

1. An apparatus to simulate biocide performance in crude oil pipeline conditions, the apparatus comprising:
   a reactor to simulate a two-phase crude oil pipeline and including a crude oil phase above a water phase, the reactor comprising an agitator to control a flow of the water phase in the reactor in response to a motor that drives an agitation rate of the agitator;
   a crude oil inlet to supply crude oil to the reactor for the crude oil phase;
   a water inlet to supply water to the reactor for the water phase;
   a control circuit configured by logic or code to:
      control a proportion of the water to the crude oil supplied to the reactor by the crude oil inlet and the water inlet, and
      control the motor to drive a desired agitation rate of the agitator;
   a biocide inlet to supply biocide to the reactor;
   a water sample outlet to sample the water phase of the reactor; and
   a plurality of coupon holders each configured to hold a corrosion coupon at a bottom of the agitated water phase of the reactor during a simulation, and to permit removing and replacing of the corrosion coupon during the simulation.

2. The apparatus of claim 1, further comprising a ball valve for each coupon holder, the ball valve being configured to seal the reactor during the removal and replacement of the corrosion coupon.

3. An apparatus to simulate oil field chemical performance in crude oil pipeline conditions, the apparatus comprising:
   a plurality of reactors each configured to simulate a two-phase crude oil pipeline and including a crude oil phase above a water phase, each reactor comprising an agitator to control a flow of the water phase in the reactor in response to a motor that drives an agitation rate of the agitator;
   a crude oil inlet to supply crude oil to each reactor for the crude oil phase;
   a water inlet to supply water to each reactor for the water phase;
   a control circuit configured by logic or code to
      independently control a proportion of the water to the crude oil supplied to each reactor by the crude oil inlet and the water inlet, and
      independently control the motor of each reactor to drive a desired agitation rate of the agitator of the reactor;
   a dedicated oil field chemical inlet for each reactor to supply an oil field chemical to the reactor; and
   a dedicated water sample outlet for each reactor to sample the water phase of the reactor.

4. The apparatus of claim 3, wherein the oil field chemical comprises at least one of a corrosion inhibitor and a biocide.

5. The apparatus of claim 3, further comprising:
   a crude oil pump to pump the crude oil from a crude oil supply to the crude oil inlet; and
   a water pump to pump the water from a water supply to the water inlet,
   wherein the control circuit controls the proportion of the water to the crude oil by controlling the crude oil pump and the water pump.

6. The apparatus of claim 3, each reactor further comprising a plurality of coupon holders each configured to
   hold a corrosion coupon at a bottom of the agitated water phase of the reactor during a simulation, and
   permit removing and replacing of the corrosion coupon during the simulation.

7. The apparatus of claim 6, further comprising a ball valve for each coupon holder, the ball valve being configured to seal the reactor during the removal and replacement of the corrosion coupon.

8. The apparatus of claim 3, wherein
   each reactor further comprises a bucket and the agitator comprises a rotor at the bottom of the bucket, the agitation rate being a rotation speed of the rotor, and
   the control circuit further controls the motor of each reactor to adjust a height of the rotor above the bottom of the bucket of the reactor.

9. The apparatus of claim 3, further comprising a dedicated height-adjustable dip tube for each reactor to obtain a mixed sample of the crude oil phase and the water phase of the reactor at an interphase region of the crude oil phase and the water phase in the reactor.

10. The apparatus of claim 3, further comprising a dedicated heating element for each reactor to heat the reactor and a dedicated temperature sensor for each reactor to sense a temperature of the reactor, wherein the control circuit is further configured by logic or code to independently control the temperature of each reactor by using the temperature sensor to sense the temperature of the reactor and by using the heating element to heat the reactor in response to the sensed temperature.

11. A method to simulate oil field chemical performance in crude oil pipeline conditions, the apparatus comprising:
   independently simulating a two-phase crude oil pipeline in each of a plurality of reactors each including a crude oil phase above a water phase;
   independently controlling, using a processing circuit, a flow of the water phase in each reactor by independently controlling a motor of an agitator of each reactor to drive a desired agitation rate of the agitator of the reactor to agitate the water phase of the reactor;
   independently supplying, using the processing circuit, crude oil to each reactor for the crude oil phase of the reactor;
   independently supplying, using the processing circuit, water to each reactor for the water phase of the reactor to reach a desired proportion of the water to the crude oil supplied to the reactor;
   independently supplying, through a dedicated oil field chemical inlet of each reactor, an oil field chemical to the reactor; and
   independently sampling, through a dedicated water sample outlet of each reactor, the water phase of the reactor.

12. The method of claim 11, wherein the oil field chemical comprises at least one of a corrosion inhibitor and a biocide.

13. The method of claim 12, wherein independently supplying the oil field chemical comprises supplying the corrosion inhibitor to one of reactors and supplying the biocide to another one of the reactors.

14. The method of claim 13, wherein independently supplying the oil field chemical further comprises supplying both the corrosion inhibitor and the biocide to yet another one of the reactors.

15. The method of claim 11, further comprising removing and replacing a corrosion coupon at a bottom of the agitated water phase of each reactor during a simulation in the reactor.

16. The apparatus of claim 11, wherein each reactor further comprises a bucket and the agitator of each reactor comprises a rotor at the bottom of the bucket, the agitation rate being a rotation speed of the rotor, and independently controlling the motor comprises independently controlling the motor of each reactor to adjust a height of the rotor above the bottom of the bucket of the reactor.

\* \* \* \* \*